Figure 1:
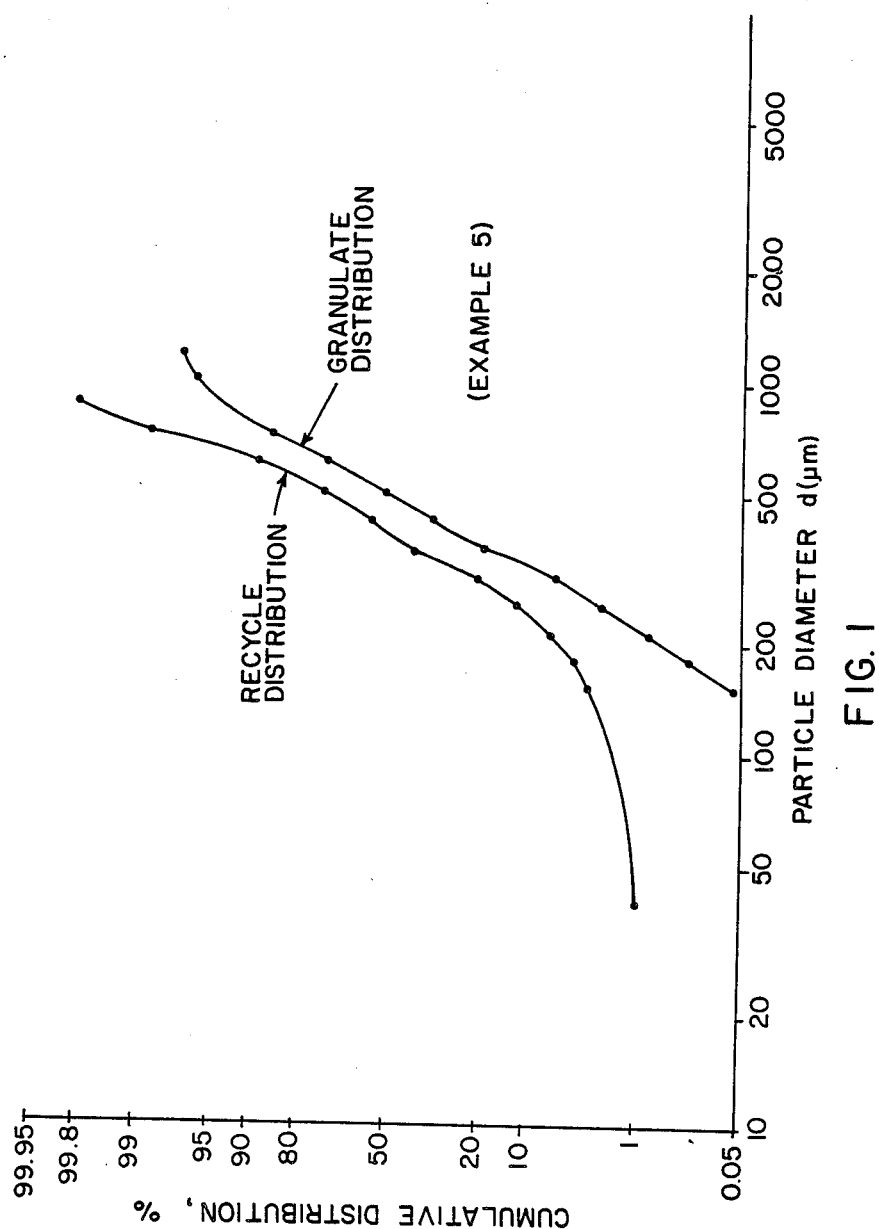

United States Patent [19]

Markussen

[11] Patent Number: 4,876,198

[45] Date of Patent: Oct. 24, 1989

[54] METHOD FOR PRODUCTION OF AN ENZYME GRANULATE

[75] Inventor: Erik K. Markussen, Vaerloese, Denmark

[73] Assignee: Novo Industri A/S, Bagsvaerd, Denmark

[21] Appl. No.: 234,180

[22] Filed: Aug. 19, 1988

[30] Foreign Application Priority Data

Aug. 21, 1987 [DK] Denmark .............................. 4355/87

[51] Int. Cl.$^4$ ................................................ C12N 9/00
[52] U.S. Cl. ...................................... 435/183; 435/187
[58] Field of Search .................................. 435/183, 187

[56] References Cited

U.S. PATENT DOCUMENTS

| | | | |
|---|---|---|---|
| 3,775,331 | 11/1973 | Borrello | 435/187 |
| 4,016,041 | 4/1977 | van Kampen | 435/187 |
| 4,087,368 | 5/1978 | Borrello | 435/187 |
| 4,106,991 | 8/1978 | Markussen | 435/187 |
| 4,661,452 | 4/1987 | Markussen | 435/187 |

*Primary Examiner*—Peter D. Rosenberg
*Attorney, Agent, or Firm*—Morris Fidelman; Franklin D. Wolffe

[57] ABSTRACT

An enzyme granulation process wherein an enzyme solution or suspension, filler, binder and cellulose or artificial fibres are granulated with fines and oversize particles of the granulate product particle the process being characterized by recirculation of fines without grinding, by grinding oversize particles then recirculation thereof, with the recirculated particles as a whole exhibiting a cumulative size distribution of the same general shape as the cumulative size distribution of the granulate product particles.

8 Claims, 2 Drawing Sheets

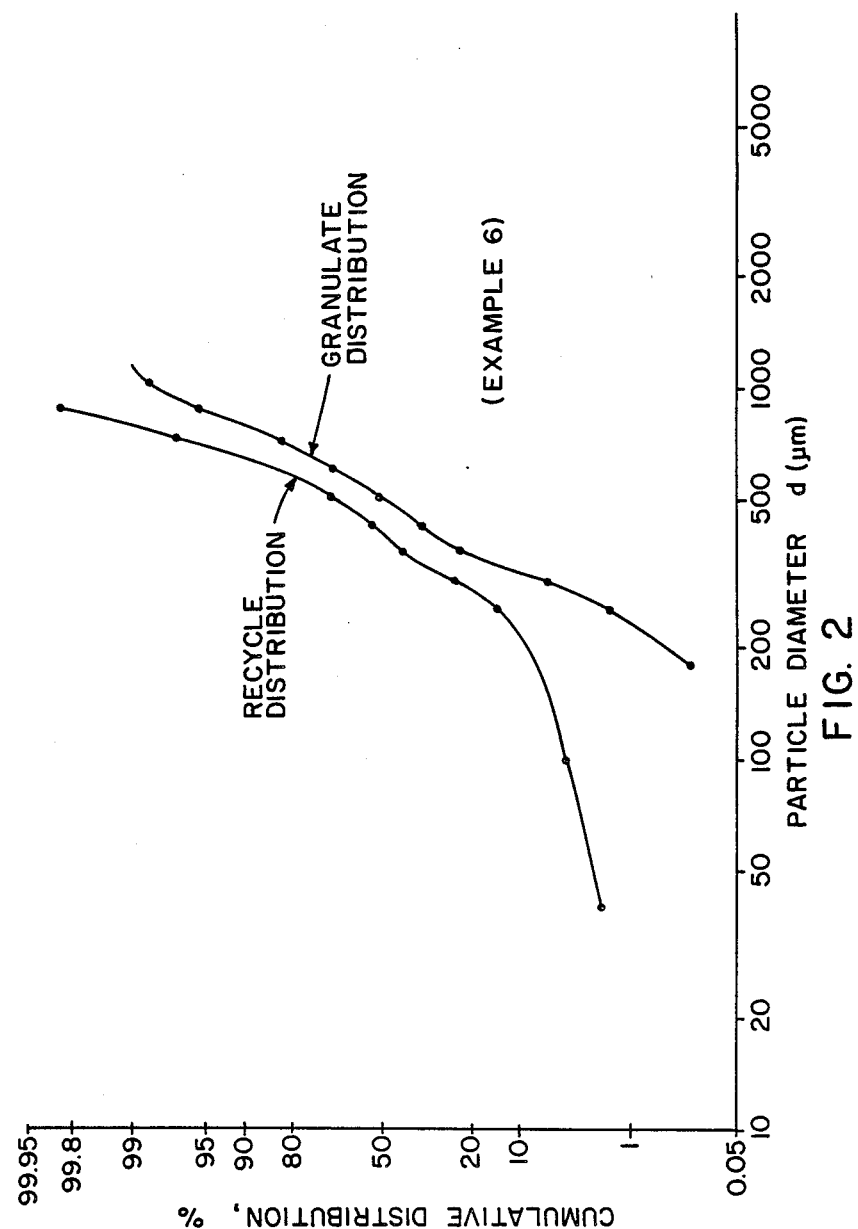

METHOD FOR PRODUCTION OF AN ENZYME GRANULATE

This invention relates to a method for production of an enzyme granulate.

BACKGROUND OF THE INVENTION

The method according to the invention is an improvement in the granulating method described in Example XVII (at column 3, lines 28–30) in U.S. Pat. No. 4,1006,991. The method of this Example is especially advantageous, because it opens the possibility of adding a liquid enzyme preparation, e.g., an ultrafiltrate, directly to the granulating drum, without necessity for first isolating the enzyme from the fermentation broth as part of a solid composition.

Even though this method for production of granulates possesses many advantageous features many characteristics of the product are open to improvement, such as a more narrow particle size distribution, higher physical strength of the granulate, and higher enzymatic activity of the granulate.

BRIEF STATEMENT OF THE INVENTION

Thus the process for production of an enzyme granulate according to the invention comprises the introduction into a granulator of from 1.5 to 40% by weight of cellulose fibres or artificial fibres, from 0 to 15% of a binder, enzyme in the form of solution or suspension of the enzyme and filler in proportion which generates the intended enzyme activity in the finished granulate, a fluid granulating agent consisting of a waxy substance and/or water, in an amount in the range of from 0 to 40% by weight, (all non-volatile ingredient percentages referring to the total amount of dry substances in the granulate). The sequence of the introduction of the different material is arbitrary, except that the major part or all of the granulating agent is introduced after substantial part (which may be all) of the dry substances are introduced in the granulator whereafter the granulate product is dried if necessary. The part of the granulate product with particle sizes outside the desired (size) interval is recirculated to the granulator with no crushing of undersized particles but with crushing of the oversized particles in such manner that overall the particle size distribution of the recycle, depicted as a cumulative particle size distribution, is the same general shape as the particle size distribution of the granulate product when depicted similarly, but displaced to the left.

Usually and preferably the enzyme in the form of a concentrated aqueous solution or suspension of the enzyme is derived directly from the fermentation broth. However, in special cases, where it is desired to avoid water, the (fermentation broth) water can be eliminated, e.g. by vacuum evaporation, and substituted by a waxy substance of the same kind as that which is used as a fluid granulating agent.

DISCUSSION OF THE INVENTION

For further understanding of this invention reference is now made to the drawing wherein:

FIG. 1 is a (log-normal distribution) graph showing the cumulative distribution of the product particles and of the recycle particles of Example 5; and FIG. 2 is the same (log-normal distribution) graph of the particles of Example 6.

Reference is made to FIGS. 1 and 2 in order to show what is meant by the expression "the same general shape". It may be seen that much of the two curves on each graph are near to parallel with the recycle particle curve being displaced (to the left) from the product particle curve about to the extent that the average particle size in the recycle is smaller. Other graphic depictions than the cumulative distribution curve on a log-normal plot herein illustrated will show comparable similarity between the product granulate and the recycle granulate. The term particle size as used herein is intended to be generally synonymous with particle diameter.

In the prior art process described by U.S. Pat. No. 4,106,991 about 20% of the oversized and undersized granules are recirculated, and both the oversized and the undersized granulates are crushed to a fine powder before recirculation. The recirculation according to the present invention, however, differs radically from this conventional recirculation, both in regard to treatment of the oversized particles and in regard to treatment of the undersized particles. According to the invention the oversized particles are crushed only to the controlled degree already indicated whereas according to prior art practices they are crushed to a fine powder (below around 100 $\mu$m). The undersized particles are not crushed at all in practice of this invention, whereas they too according to prior art practices are crushed to a fine powder (below around 100 $\mu$m). Surprisingly, this changed recirculation scheme exerts a strong influence on the characteristics of the enzyme granulates. The enzyme granulate produced by means of the method according to the present invention possess both much narrower particle size distribution and much better physical strength. Also, it has been found that the particle size distribution can be controlled much easier by means of the method according to the invention.

Recirculation normally is done with the particles with "wrong" particle size, i.e., oversize and undersize. However, particles of "right" particle size may be recirculated, if such happens to be appropriate.

The method according to the invention can be performed both batchwise and continuously.

MATERIALS EMPLOYED FOR THE GRANULATE

The cellulose in fibrous form can be sawdust, pure fibrous cellulose, cotton, or other forms of pure or impure fibrous cellulose.

Several brands of cellulose in fibrous form are on the market, e.g., CEPO and ARBOCEL. In a publication from Svenska Tramjolsfabrikerna AB, "Cepo Cellulose Powder" it is stated that for Cepo S/20 cellulose the approximate maximum fibre length is 500$\mu$, the approximate average fibre length is 160$\mu$, the approximate maximum fibre width is 50$\mu$ and the approximate average fibre width is 30$\mu$. Also it is stated that CEPO SS/200 cellulose has an approximate maximum fibre length of 150$\mu$, an approximate average fibre length of 50$\mu$, an approximate maximum fibre width of 45$\mu$ and an approximate average fibre width of 25$\mu$. Cellulose fibres with these dimensions are very well suited for the purpose of the invention.

Typical synthetic fibres which may be used instead of the cellulose are made of polyethylene, polypropylene, polyester, especially Nylon, polyvinylformal, and poly(meth)acrylic compounds. For convenience all such non-cellulose fibres have been termed artificial fibres.

The binders used in the process according to the invention are the binders conventionally used in the field of granulation with a high melting point or with no melting point at all and of a non waxy nature, e.g., polyvinyl pyrrolidone, dextrins, polyvinylalcohol, and cellulose derivatives, including for example hydroxypropyl cellulose, methyl cellulose or CMC. The binders can be added in the solid state or in liquid form, as appropriate to the binder. A granulate cannot be formed on the basis of cellulose, enzyme filler and a binder, as above defined, without the use of a granulating agent, such as is described below.

All enzymes can be granulated by means of the process according to the present invention. Preferably, proteinases, amylases, lipases oxidases and cellulases are granulated according to the invention. Specific examples are ALCALASE ® (a Bacillus licheniformis proteinase), ESPERASE ® and SAVINASE ® (microbial alcaline proteinases produced according to the British Pat. No. 1,243,784) and TERMAMYL ® (a Bacillus licheniformis amylase). The enzyme is introduced into the granulator as a solution, for example, a concentrated enzyme solution prepared by ultrafiltration, reverse osmosis or evaporation. On occasion it is not certain whether the enzyme is truly in solution or is in suspension. In any event, enzymes suspended in water or solvent as well as enzymes dissolved in water or solvent may be granulated in practice of this invention.

The filler is used as a component in the granulate only for the purpose of adjusting the intended enzyme activity in the finished granulate. Since the enzyme (fermentation broth) concentrate introduced into the granulator already contains diluent impurities which may be considered to constitute fillers, additional filler is not always needed to standardize the enzymatic activity of the granulate. The filler material when used is usually organic or inorganic salts, and they need not be soluble in water, e.g., $Na_2SO_4$, $NaCl$, $CaCO_3$, or finely divided minerals, silicates, e.g., kaolin or bentonite. Other inert fillers which do not interfere with the granulating process and the intended use of the granulate product can be used.

The granulating agent may be water and/or a waxy substance. The granulating agent is always in liquid phase during the granulation process. The waxy substance when present, therefore, is either dissolved or dispersed in the water or is melted. By a waxy substance is understood a substance which possesses all of the following characteristics: (1) the melting point is between 30° and 100° C., preferably between 40° and 80° C., (2) the substance is of a tough and not brittle nature, and (3) the substance possesses substantial plasticity at room temperature.

Both water and waxy substance are granulating agents, i.e., they are both active during the formation of the granules, the waxy substance remains as a constituent in the finished granules, whereas the water is removed during drying. Thus, in order to refer all proportions to the finished, dry granules all percentages herein provided are calculated on the basis of total dry substances, which means that water, when one of the granulating agents, is not added to the other constituents when calculating the percentage of water used, whereas a waxy substance granulating agent, has to be added to the other dry constituents in the granulate when calculating the percentage of waxy substance. Examples of waxy substances are polyglycols, fatty alcohols, ethoxylated fatty alcohols, higher fatty acids, mono-, di- and triglycerolesters of higher fatty acids, e.g., glycerol monostearate, alkylarylethoxylates, and coconut monoethanolamide.

If a high amount of waxy substance is used, relatively little water should be added, and vice versa. Thus, the granulating agent can be either water alone, waxy substance alone or a mixture of water and waxy substance. In case a mixture of water and waxy substance is used, the water and the waxy substance can be added in any sequence, e.g., first the water and then the waxy substance, or first the waxy substance and then the water or a solution or suspension of the waxy substance in the water. Also, in case a mixture of water and waxy substance is used, the waxy substance can be soluble or insoluble (but dispersable) in water.

If no water is used in the granulating agent, and the solution or suspension of enzyme is on a non-aqueous basis, usually no drying is needed. In this instance the granulating agent usually is a melted waxy material, and only cooling is needed to solidify the granulate particles. In most instances, however, some drying is performed, and the drying usually is carried out as a fluid bed drying wherein small amounts of dust and small granules are blown away from the surface of the granules. However, any kind of drying can be used. Also, in the instance where no water is used as a granulating agent, and when the solution or suspension of enzyme is non-aqueous, a flow conditioner or anticaking agent may be added to the granulate either before or after the cooling step, e.g., fumed silica, for instance the commercial products AEROSIL or CAB-O-SIL.

The relative amount of fluid enzyme and fluid granulating agent determines the particle sizes of the finished enzyme granulate: the higher the relative amount of fluid is, the bigger the particle sizes will be. The higher the relative amount of added cellulose is, the more fluid can be absorbed. The skilled worker will know when to dry during the granulation process and to what extent. Granulation per se is a well known process and the detailed practice thereof as such forms no part of this invention.

The granulator can be any of the known types of mixing granulators, drum granulators, pan granulators or modifications of these. If a mixing granulator issued, for example a mixing drum from the German Company Gebr. Lodige Maschinen G.m.b.H, 479 Paderborn, Elselnerstrasse 7-9, DT; it is preferred, however, that small rotating knives are mounted in the granulator in order to compact the granules.

Furthermore, facultative additives as coloring agents, pigments, disintergants, or enzyme stabilizers, e.g., antioxidants, may be incorporated in the granulate.

An especially important facultative additive is a water absorbent agent, e.g., Bentonite or diatomaceous earth, which opens up the possibility for the addition of more enzyme solution, and thus obtainment of a granulate product with a higher specific activity than is otherwise obtained.

In a preferred embodiment of the method according to the invention the cellulose fibres or the artificial fibres have an average fibre length of 50–2000 μm, preferably 100–1000 μm, and an average fibre width of 20–50 μm, preferably 25–40 μm. Hereby a satisfactory mechanical strength is obtained.

In a preferred embodiment of the method according to the invention the amount of cellulose fibres or artificial fibres is between 4 and 20% by weight, based on the dry weight of the granulate. Below 4% by weight of fibres no satisfactory fiber effect is obtained, and above 20% by weight of fibres production of the granulate becomes cumbersome and the granulate product more expensive.

In a preferred embodiment of the method according to the invention the enzyme is a protease, an amylase, a lipase, a cellulase, or an oxidase. These are the most common enzymes offered in granulate form for industrial purposes.

In a preferred embodiment of the method according to the invention the filler consists of or comprises inorganic salts. Thereby an inexpensive granulate is obtained.

In a preferred embodiment of the method according to the invention between 10 and 90% of the product granulate is recirculated. At a recirculation rate of below 10% it is difficult to obtain satisfactory particle strength, and at a recirculation above 90% the process as a whole becomes uneconomic due to loss of enzyme activity.

In a preferred embodiment of the method according to the invention the granulation is performed at temperature between 20° and 70° C. At a temperature below 20° C. cooling of the granulator often will be necessary, and at a temperature above 70° C. the enzyme will often lose activity.

Practice of the invention will be illustrated by the following examples.

The activity units used in the examples are defined as follows.

| enzyme | Activity unit | Definition indicated in |
| --- | --- | --- |
| proteolytic | KNPU | AF 220/1-GB |
| amylolytic | KNU(T) | AF 214/1 GB |
| lipolytic | LU | AF 95/4-GB |
| cellulolytic | CMCU | AF 187/3-GB |

On request these AF publications can be obtained from NOVO INDUSTRI A/S, Novo Allé, 2880 Bagsvaerd, Denmark.

EXAMPLE 1

9.0 kg of a recycled granulate produced according to this example, and consisting of 1.5 kg of unground fines (<300 μm) and 7.5 kg of product fraction (300–710 μm) is introduced into a Lödige mixer FM 50 with
  1.5 kg of fibrous cellulose, Arbocel BC 200
  0.4 kg of TiO$_2$, and
  7.0 kg of ground Na$_2$SO$_4$ The mixed dry components are sprayed with 4.8 kg of fluid Savinase concentrate (25 KNPU/g), produced by ultrafiltration and evaporation. The viscosity of the concentrate at 18° C. is 80 cP, measured with a Brookfield RVT viscosimeter, spindle 1, 50 rpm. During and after the spraying the moist mixture is exposed to a compacting and granulating influence from the multiple set of knives, as described in Example 1 of U.S. Pat. No. 4,106,991. When the granulation is finished, the granulate is dried on a fluid bed, and the part thereof defined as product fraction (in this case 300–710 μm) is separated for quality testing. The undesize fraction, which is not treated, and the oversize fraction which is crushed to a cumulative particle size distribution, which is of the same general shape as the cumulative particle size distribution of the product fraction, but displaced to the left, such as is shown on FIGS. 1 and 2, are recirculated.

EXAMPLE 2

This Example is a comparison example corresponding to the process described in U.S. Pat. No. 4,106,991.
  3.0 kg of fibrous cellulose, Arbocel BC 200
  0.8 kg of TiO$_2$, and
  14.8 kg of ground Na$_2$SO$_4$
is mixed in a Lödige mixer FM 50, and is sprayed with 6.3 kg of a Savinase ultrafiltrate, concentrated by evaporation, with an activity of 25 KNPU/g, followed by a granulation treatment, as described in Example 1. Subsequently the granulate is dried on a fluid bed.

The following grain size distributions were obtained for the granulates obtained from Examples 1 and 2:
Particle size distribution:

| | Example 1 | Example 2 |
| --- | --- | --- |
| >1000 μm | 2% | 9% |
| >850 μm | 4% | 16% |
| >710 μm | 15% | 29% |
| >600 μm | 31% | 45% |
| >500 μm | 53% | 60% |
| >420 μm | 66% | 73% |
| >355 μm | 79% | 86% |
| <300 μm | 10% | 8% |
| <250 μm | 4% | 3% |
| Mean diameter | 510 μm | 560 μm |
| 300–710 μm fraction | 81% | 68% |

The above particle size distribution and the above mean diameter as well as all other particle size distributions and mean diameters herein described is on a weight basis.

The amount of dust and the physical strength are measured according to two different methods:
  A. Elutriation dust method, as described in NOVO publication AF 129/3-GB, available on request from NOVO INDUSTRI A/S.
  B. Novo attrition dust method, as described in NOVO publication AF 225/1-GB, available on request from NOVO INDUSTRI A/S.

It appears from the following table that the values in regard to dust and physical strength of the granulate according to Example 1 is superior to the corresponding prior art values (Example 2).

| | Example 1 (invention) | | Example 2 (prior art) | |
| --- | --- | --- | --- | --- |
| Method | total, mg | active, μg (4 KNPU/g) | total, mg | active, μg (4 KNPU/g) |
| A | 13.2 | 10700 | 89.7 | 81500 |
| B | 7.2 | 4200 | 56.0 | 43100 |
| | activity: 7.9 KNPU/g | | activity: 6.9 KNPU/g | |

EXAMPLE 3

9.5 kg of a recycled granulate produced according to this example, and consisting of 1.6 kg of unground fines (<300 μm) and 7.9 kg of product fraction (300–710 μm) is introduced into a Lödige mixer FM 50 with
  1.43 kg of fibrous cellulose, Arbocel BC 200
  0.38 kg of TiO$_2$, and
  6.36 kg of ground Na$_2$SO$_4$ The mixed dry components are sprayed with 4.7 kg of Savinase ultrafiltrate, concentrated by evaporation, with an activity of 26 KNPU/g, and wherein 200 g of a carbohydrate binder is dissolved. The moist mixture is treated, granulated and dried as indicated in Example 1.

EXAMPLE 4

This example is a comparison example corresponding to the process described in U.S. Pat. No. 4,106,991.
3.0 kg of fibrous cellulose, Arbocel BC 200
0.8 kg of TiO₂, and
13.8 kg of ground Na₂SO₄
is granulated and dried as described in Example 2, but with addition of 5.7 kg of a Savinase ™ ultrafiltrate, concentrated by evaporation, with an activity of 26 KNPU/g, and wherein 400 g of a carbohydrate binder is dissolved.

The following particle size distributions were obtained for the granulates produced according to Examples 3 and 4.

Particle size distribution:

|  | Example 3 | Example 4 |
| --- | --- | --- |
| >1000 μm | 2.7% | 10% |
| >850 μm | 5.7% | 20% |
| >710 μm | 17% | 32% |
| >600 μm | 35% | 49% |
| >500 μm | 56% | 64% |
| >425 μm | 68% | 76% |
| >355 μm | 77% | 83% |
| <300 μm | 12% | 10% |
| <250 μm | 5.8% | 5.6% |
| Mean diameter | 520 μm | 600 μm |
| 300–710 μm fraction | 71% | 58% |

It appears from the following table that the values in regard to dust and physical strength of the granulate according to Example 3 are superior to the corresponding prior art values (Example 4).

| | Example 1 (invention) | | Example 2 (prior art) | |
| --- | --- | --- | --- | --- |
| Method | total, mg | active, μg (4 KNPU/g) | total, mg | active, μg (4 KNPU/g |
| A | 9.8 | 4100 | 109.5 | 30100 |
| B | 9.8 | 3500 | 150.5 | 52400 |
| | activity: 9.4 KNPU/g | | activity: 7.8 KNPU/g | |

EXAMPLE 5

13.4 kg of a recycled granulate produced according to this example, and consisting of 2.6 kg of unground fines (<300 μm), 8.1 kg of product fraction (300–710 μm), and 2.7 kg of moderately ground oversized fraction (originally >710 μm) is introduced into a Lödige mixer FM 50 with
1.0 kg of fibrous cellulose, Arbocel BC 200
0.26 kg of TiO₂, and
4.5 kg of ground Na₂SO₄
The mixed, dry components are sprayed with 4.0 kg of fluid Savinase concentrate (24 KNPU/g), produced by ultrafiltration and evaporation. The moist mixture is treated, granulated and dried as indicated in Example 1.

The following grain size distribution was obtained:
Particle size distribution:

| | |
| --- | --- |
| 3.6% | >1000 μm |
| 6.0% | >850 μm |
| 14.0% | >710 μm |
| 28.0% | >600 μm |
| 49.0% | >500 μm |

-continued

| | |
| --- | --- |
| 67.0% | >425 μm |
| 81.0% | >355 μm |
| 6.0% | <300 μm |
| 2.3% | <250 μm |
| Mean diameter | 495 μm |
| 300–710 μm fraction | 80% |

The values for the amount of dust and physical strength of the 300–710 μm fraction of the granulate appear from the following table.

| Method | total, mg | active, μg (4 KNPU/g) |
| --- | --- | --- |
| A | 1.3 | 650 |
| B | 3.0 | 2330 |

Reference is made to FIG. 1 for graph depiction of the particle size distribution of the granulate product and the recycle.

EXAMPLE 6

10.0 kg of a recycled granulate produced according to this example, and consisting of 2.0 kg of unground fines (<300 μm), 4.0 kg of product fraction (300–710 μm), and 4.0 kg of moderately ground oversized particles (originally >710 μm) is introduced into a Lödige mixer FM 50 with
1.5 kg of fibrous cellulose, Arbocel BC 200
1.0 kg of Perlite BF
0.4 kg of TiO₂, and
5.4 kg of ground Na₂SO₄
The mixed, dry components are sprayed with 5.3 kg of fluid Savinase concentrate (13 KNPU/g), produced by ultrafiltration and evaporation. The moist mixture is treated, granulated and dried as indicated in Example 1.

The following grain size distribution was obtained:
Particle size distribution:

| | |
| --- | --- |
| 1.7% | >1000 μm |
| 4.5% | >850 μm |
| 18.0% | >710 μm |
| 32.0% | >600 μm |
| 49.0% | >500 μm |
| 65.0% | >425 μm |
| 77.0% | >355 μm |
| 6.0% | <300 μm |
| 1.7% | <250 μm |
| Mean diameter | 495 μm |
| 300–710 μm fraction | 76% |

The values for the amount of dust and physical strength of the 300–710 μm fraction of the granulate appear from the following table.

| Method | total, mg | active, μg (4 KNPU/g) |
| --- | --- | --- |
| A | 11.2 | 2300 |
| B | 8.9 | 3900 |
| | activity: 8.3 KNPU/g | |

Reference is made to FIG. 2 for graph depiction of the particle size distribution of the granulate product and the recycle.

EXAMPLE 7

10.0 kg of a recycled granulate produced according to this example and consisting of 2.5 kg of unground fines (<425 μm), 5.0 kg of product fraction (425-630 μm) and 2.5 kg of moderately ground oversized fraction (originally >630 μm) is introduced into a Lödige mixer FM 50 with 1.5 kg of fibrous cellulose, Arbocel BC 200
1.0 kg of Clarcel CBL-3 diatomaceous earth
0.4 kg of TiO$_2$, and
5.4 kg of ground Na$_2$SO$_4$ The mixed dry components are sprayed with 4.8 kg of a Savinase ultrafiltrate, concentrated by evaporation, with an activity of 19 KNPU/g. The moist mixture is treated, granulated and dried as indicated in Example 1.

EXAMPLE 8

This example is a comparison example corresponding to the process described in U.S. Pat. No. 4,106,991.

3.0 kg of fibrous cellulose, Arbocel BC 200
0.8 kg of TiO$_2$
2.0 kg of Clarcel CBL-2 diatomaceous earth, and
14.4 kg of ground Na$_2$SO$_4$ is granulated with 6.6 kg of ultrafiltered Savinase concentrate, concentrated by evaporation and with an activity of 17 KNPU/g, and dried as described in Example 2.

The following particle size distributions were obtained for the granulates obtained from Examples 7 and 8:

Particle size distribution:

|  | Example 7 | Example 8 |
|---|---|---|
| >1000 μm | 5% | 18% |
| >850 μm | 11% | 27% |
| >710 μm | 30% | 39% |
| >600 μm | 49% | 52% |
| >500 μm | 66% | 66% |
| >425 μm | 77% | 76% |
| >355 μm | 85% | 84% |
| <300 μm | 6.0% | 8% |
| <250 μm | 2.2% | 3.5% |
| Mean diameter | 590 μm | 610 μm |

It appears from the following table that the values in regard to dust and physical strength of the granulate according to Example 7 are superior to the corresponding prior art values (Example 8).

| | Example 7 (invention) | | Example 8 (prior art) | |
|---|---|---|---|---|
| Method | total, mg | active, μg (4 KNPU/g) | total, mg | active, μg (4 KNPU/g) |
| A | 2.0 | 1090 | 95.6 | 25200 |
| B | 1.3 | 650 | 28.6 | 11600 |
| | activity: 8.2 KNPU/g | | activity: 5.2 KNPU/g | |

EXAMPLE 9

10.0 kg of a recycled granulate produced according to this example, and consisting of 1.0 kg of unground fines (<300 μm) and 9.0 kg of product fraction (300-900 μm) is introduced into a Lödige mixer FM 50 with 1.5 kg of fibrous cellulose, Arbocel BC 200
1.0 kg of Perlite BF
0.4 kg of TiO$_2$, and
4.7 kg of ground Na$_2$SO$_4$ The mixed dry components are sprayed with 5.5 kg of a Humicola insolens cellulase ultrafiltrate, concentrated by evaporation, with an activity of 4630 CMCU/g and a viscosity of 117 cP at 19.5° C., and to which 0.5 kg of carbohydrate binder is admixed. The starting material for the fluid cellulase concentrate is produced as indicated in U.S. Pat. No. 4,435,307. The moist mixture is treated, granulated and dried as indicated in Example 1.

The following particle size distribution was obtained:

Particle size distribution:

| | |
|---|---|
| 4.5% | >1000 μm |
| 16% | >850 μm |
| 34% | >710 μm |
| 52% | >600 μm |
| 70% | >500 μm |
| 81% | >425 μm |
| 89% | >355 μm |
| 2.2% | <300 μm |
| 0.8% | <250 μm |
| Mean diameter | 615 μm |
| 300-900 μm fraction | 87% |

The values for the amount of dust and physical strength of the granulate appear from the following table.

| Method | total, mg | active, μg (2400 CMCU/g) |
|---|---|---|
| A | 10.6 | 1600 |
| B | 2.5 | 760 |
| | activity: 2600 CMCU/g | |

EXAMPLE 10

20 kg of a recycled granulate produced according to this example, and consisting of 7 kg of unground fines (<300 μm) and 13 kg of product fraction (300-900 μm) is introduced into a Lödige mixer FM 130 together with 3.0 kg of fibrous cellulose, Diacel 200
2.1 kg of carbohydrate binder
13.6 kg of ground Na$_2$SO$_4$ A fluid lipase concentrate with an activity of 496.000 LU/g and a viscosity of 200 cP at 21° C. was produced by fermentation according to Danish patent application No. 4499/87 followed by concentration by ultrafiltration and evaporation.

The mixed dry components indicated above were sprayed with 8.0 kg of the fluid concentrate indicated above. The thus produced, moist mixture is treated, granulated and dried as described in Example 1.

The following particle size distribution was obtained:

| | |
|---|---|
| 4.1% | >1180 μm |
| 9.1% | >1000 μm |
| 18.9% | >850 μm |
| 31.7% | >710 μm |
| 43.1% | >600 μm |
| 57.3% | >500 μm |
| 67.2% | >425 μm |
| 75.6% | >355 μm |

|  |  |  |
|---|---|---|
|  | 88.3% | >300 μm |
|  | 4.6% | <250 μm |
| Mean diameter |  | 550 μm |

Product properties: Activity: 155.000 LU/g
Dust properties (300–900 μm fraction):

|  |  | Total | Active/μg of 155.000 LU/g |
|---|---|---|---|
| Method: | A: | 15.5 mg | 650 μg |
|  | B: | 7.1 mg | 1340 μg |

EXAMPLE 11

5 kg of Termamyl ™ granulate produced according to this example is used as the recirculation material. These 5 kg of Termamyl ™ granulate consist of fines (<300 μm), product fraction (300–900 μm) and ground oversize fraction. The recirulation material is introduced into a Lödige mixer type FM 130 together with the following granulation components:

3.0 kg of cellulose fibres
0.6 kg of titanium dioxide
2.1 kg of carbohydrate binder
18.3 kg of $Na_2SO_4$ A fluid Termamyl ™ concentrate with an activity of 550 KNU(T)/g and a dry matter content of approximately 30% was produced by fermentation according to U.S. Pat. No. 3,912,590 and DK Pat. No. 123726, followed by concentrtion by ultrafiltration and evaporation.

The mixed dry components indicated above were sprayed with 6.8 kg of the fluid Termamyl concentrate indicated above. The thus produced moist mixture is treated, granulated and dried as described in Example 1.

The following particle size distribution was obtained:

|  |  |
|---|---|
| 9.0% | >1200 μm |
| 14.8% | >1000 μm |
| 22.9% | >850 μm |
| 33.0% | >710 μm |
| 43.9% | >600 μm |
| 57.3% | >500 μm |
| 67.5% | >425 μm |
| 13.9% | <300 μm |

| Activity: 133.7 KNU(T)/g | Water content: 0.7% |
|---|---|
| Dust measurement: |  |
| Method A: total mg 9.5 | 1950 μg Termamyl 60 KNU(T)/g |
| Method B: total mg 7.3 | 1100 μg Termamyl 60 KNU(T)/g |

I claim:

1. In a process for production of an enzyme granulate which comprises granulating an enzyme composition comprising enzyme, filler, binder, and from 1.5–40% by weight thereof of cellulose or artificial fibers, the enzyme added to the granulating process being in solution or suspension, and wherein the granulate product particles are separated into a middle fraction containing particles of the desired size interval, a small size fraction containing particles smaller than the desired size interval, and a large size fraction containing particles larger than the desired size interval with said small size and large size fractions being recirculated to the granulating process, the improvement which comprises:

recirculating the particles of said small size fraction without grinding of same, and grinding the particles of said large size fraction then recirculating same, the particles of said large size fraction being ground so that the recirculated particles as a whole exhibit a cumulative particle size distribution curve of the same general shape as the cumulative particle size distribution curve of the aforesaid granulate product particles.

2. The process of claim 1 wherein the large size and small size particles recirculated comprise from 10–90% by weight of the aforesaid granulate product particles.

3. The process of claim 1 further comprising a desired particle size interval of about 300–900 μm.

4. The process of claim 1 wherein granulation is performed at a temperature between 20° and 70° C.

5. The process of claim 1 wherein the enzyme is a protease, an amylase, a cellulase, a lipase or an oxidase.

6. The process of claim 1 wherein the granulate product particles are dried prior to separation into said fractions.

7. The process of claim 1 wherein the fiber content comprises 4–20% by weight.

8. The process of claim 1 wherein the enzyme composition contains a waxy substance granulating agent.

* * * * *

UNITED STATES PATENT AND TRADEMARK OFFICE
CERTIFICATE OF CORRECTION

PATENT NO.  : 4,876,198
DATED       : October 24, 1989
INVENTOR(S) : Erik K. Markussen It is certified that error appears in the above-identified patent and that said Letters Patent is hereby corrected as shown below:

Col. 1, line 12, "4,1006,991" should read -- 4,106,991 --.
Col. 1, line 46, "overall the" should read -- the overall --.
Col. 1, line 48, "is" should read -- has --.
Col. 4, line 52, "disintergants" should read -- disintegrants --.
Col. 4, line 55, "Bentonite" should read -- bentonite --.
Col. 11, line 18, "recirulation" should read -- recirculation --.

Signed and Sealed this

Third Day of November, 1992

*Attest:*

DOUGLAS B. COMER

*Attesting Officer*   Acting Commissioner of Patents and Trademarks